United States Patent [19]

Kane et al.

[11] 4,283,347

[45] Aug. 11, 1981

[54] PARA-MENTH-1-ENE-7-SULFONIC ACID AND SALTS THEREOF

[75] Inventors: Bernard J. Kane, Atlantic Beach; Sean G. Traynor, Jacksonville, both of Fla.

[73] Assignee: SCM Corporation, New York, N.Y.

[21] Appl. No.: 125,151

[22] Filed: Feb. 27, 1980

Related U.S. Application Data

[60] Division of Ser. No. 29,858, Apr. 13, 1979, Pat. No. 4,224,240, which is a continuation of Ser. No. 879,127, Feb. 21, 1978, abandoned.

[51] Int. Cl.$^3$ ............................................. C07C 143/22
[52] U.S. Cl. ............................. 260/429.9; 260/448 R; 260/501.19; 260/501.21; 260/503
[58] Field of Search .............. 260/503, 501.19, 501.21, 260/429.9, 448 R

[56] References Cited

U.S. PATENT DOCUMENTS

| 3,867,432 | 2/1975 | Bloch | 260/503 |
| 4,137,257 | 1/1979 | Traynor | 260/503 |

OTHER PUBLICATIONS

Bordwell et al., JACS, 79, 3493, (1957).

*Primary Examiner*—Nicky Chan
*Attorney, Agent, or Firm*—Merton H. Douthitt; Gordon P. Becker

[57] ABSTRACT

Para-menth-1-ene-7-sulfonate salts are made by reacting $\beta$-pinene with a bisulfite salt under free radical conditions.

4 Claims, No Drawings

PARA-MENTH-1-ENE-7-SULFONIC ACID AND SALTS THEREOF

This is a division of application Ser. No. 029,858, filed Apr. 13, 1979, now U.S. Pat. No. 4,224,240, which is a continuation of application Ser. No. 879,127, filed Feb. 21, 1978, now abandoned.

BACKGROUND OF THE INVENTION

The present invention relates to the preparation of para-menth-1-ene-7-sulfonate salts and more particularly to their preparation from the bicyclic terpene, β-pinene.

Reactions of α-, and β-pinene with various sulfur-containing compounds have been reported to lead to a diversity of products dissimilar in the terpene structure. For instance, Bordwell and Hewitt report that alpha-pinene and beta-pinene react with thioacetic acid under the influence of ultraviolet irradiation to give 3-pinanyl and 10-pinanyl thioacetate, respectively. The authors report that no para-menthene products could be found in the respective products. (*Journal of American Chemical Society*, Vol. 79, pages 3493-3496, 1957). Buess et al report that alpha-, and beta-pinene react with mercaptoacetic acid to give compounds of undetermined structure in the presence of peroxides and ultraviolet radiation (*J. Org. Chem.*, Vol. 22, pages 197-200, 1957). Gaiffe and Castanet, however, report that alpha-, and beta-pinene do react with thioacetic acid and mercaptoacetic acid to produce para-menthene thioacetates and para-menthene mercaptoacetic acids, respectively, in the presence of di-t-butyl peroxide. These authors report similar results with mercaptoacetic acid, 2-hydroxyethane thiol, thiophenol, 2-mercapto-propionic acid, and methyl mercaptoacetate. (*C. R. Acad. Soc. Paris*, Vol. 271, Series C, pages 1012-1014, 1970). Further, Warner reports that β-pinene will react with hydrogen sulfide to give a 10-pinanyl mercaptan (U.S. Pat. Nos. 3,114,776 and 3,248,315). It should be noted too that the reaction of a linear olefin with sodium bisulfite, for example often produces a mixture of the olefin sulfinate-sulfonate and the olefin sulfonate (eg. see Bright et al, *J. Appl. Chem. Biotechnol.*, 25, pp. 901-912, 1975).

Certainly in view of the foregoing citations, reaction products of bicyclic terpenes, in general, and β-pinene in particular, with sulfur-containing compounds cannot be predicted with certainty nor with accuracy. The present invention relates to para-menth-1-ene-7-sulfonate salts useful as surfactants and their corresponding para-menth-1-ene-7-sulfonic acids potentially useful as resolving agents, which sulfonate salts are prepared from beta-pinene.

BROAD STATEMENT OF THE INVENTION

The present invention is a process for making para-menth-1-ene-7-sulfonate salt from β-pinene. The process comprises maintaining an aqueous reaction mixture of β-pinene and a bisulfite salt under free radical conditions until the para-menth-1-ene-7-sulfonate salt is formed. This reaction is carried out at a temperature of at least about 50° C. and preferably between about 50° and 300° C.

DETAILED DESCRIPTION OF THE INVENTION

The sulfonating agent is a bisulfite salt. Suitable bisulfites can be salts of alkali metals which include sodium, potassium, lithium, rubidium, and cesium; alkaline earth metals including calcium, strontium, barium, and magnesium; various amines such as, for example, triethanolamine; zinc, and aluminum and the like. The bisulfite salts are solubilized in the reaction mixture by water and, therefore, some water solubility of the bisulfite salt is preferred. Generally there is from about 0.1 to 10 moles of bisulfite salt per mole of β-pinene in the reaction mixture and preferably from about 0.5 to 5 moles.

Free radical conditions in the reaction mixture are established by the addition of a free radical initiator to the reaction mixture. Preferably, the free radical initiator is gaseous oxygen typically at a partial pressure ranging from as low as about 1 psig up to as high as about 400 psig, though a wide variety of conventional free radical initiators can be used in the present process. Representative of these free radical initiators include various peroxides such as tert-butyl peroxide, hydrogen peroxide, benzoyl peroxide, cumene hydroperoxide, tetralin hydroperoxide, diisopropyl benzene hydroperoxide, acetyl peroxide, urea peroxide, methyl ethyl ketone peroxide, diisopropyl ether peroxide, and the like and mixtures thereof; tert-butyl perbenzoate, diisopropyl peroxy dicarbonate, hexachloroethane/tetraborate (1%/1%), hydrazine sulfate (3%), sodium persulfate/sodium tetraborate (1%/1%), dibenzoylhydrozine (5%), tetraethyllead (3%), azobisisobutyronitrile, and the like, and mixtures thereof. Generally, from about 0.1 to about 10 mole-% (basis β-pinene) of the free radical initiator is used in the reaction mixture. Additionally, ultraviolet radiation may serve to establish the free radical conditions, including when a UV photoinitiator is added to the reaction mixture.

Conventional organic cosolvents non-reactive in the process preferably are used in the reaction mixture. Such solvents include alcohols, ethers, cellosolves, esters, glycols, amines, aminoalcohols, and the like and mixtures thereof. Preferable an aqueous solvent is used in the instant process. By aqueous solvent, it is meant that at least about 1% by weight of the solvent is water and this can range up to virtually 100% water, though preferably some organic cosolvent is used to assist in adequately pulling the β-pinene into the aqueous reaction mixture. The water is used to assist in the solubilizing of the bisulfite salt in the reaction mixture. Preferably solvents include, for example, methanol, ethanol, isopropanol, and similar alkanols. Equal volumes of water and organic cosolvent are advantageous for the present process and preferably equal volumes of a $C_{1-10}$ alkanol and water are used.

The reaction is conducted at a temperature of at least about 50° C. and broadly the temperature can be from about 50° to 300° C. and preferably between about 100° and 150° C. The reaction can be conducted at atmospheric pressure, subatmospheric pressure, or super atmospheric pressure as is necessary, desirable, or convenient.

It can be quite advantageous on occasion to enhance the conversion of β-pinene to the para-menth-1-ene-sulfonate salt by inclusion of certain nitrate catalysts such as the nitrates of sodium, lithium, potassium, ammonium, zinc, cadmium, chromium, bismuth, aluminum, and alkaline earth metals. Typically from about 0.01 to 1 mole of catalyst per mole of β-pinene is included in the reaction mixture and preferably from about 0.05 to 0.5 moles. Other catalysts which can be advantageously used to enhance the reaction conversion in the instant process include catalysts containing the anions: nitrites, halides, sulfates, acid sulfates, phosphates, acid phosphates, carbonates, bicarbonates, borates, silicates, carboxylates, alkylsulfonates, alkyl phosphates and the like and mixtures thereof. The anion of the catalyst appears to be the influential portion of the catalyst in the present process and, thus, a wide variety of cations can be used with the foregoing preferred anions. Suitable cations can be chosen from Subgroup 1(a) alkali metals and their ammonium and alkylammonium and arylammonium analogs; Subgroup 2(a) alkaline earth metals; Subgroup 3(a) metals; Subgroup 4(a) metals; Subgroup 1(b) metals; Subgroup 2(b) metals; Subgroup 3(b) metals; and first row "transition series" metals; especially, iron, cobalt, nickel, and preferably zinc, but excluding copper which is deleterious to the bisulfite salts.

In practicing the present process with the aid of the indicated catalysts, the conversion of β-pinene to the desired sulfonate salts generally will range from about 1% to about 30%. When using the preferred nitrate catalysts, however, conversions can be increased to about 50% to 90+% typically. It should be noted that the product sulfonate salts are recovered in hydrated form so that their complete recovery from the aqueous reaction mixture often may be difficult. Even with fairly exhaustive recovery and work-up procedures some loss of the product may be expected. Reaction times for the process can be as little as a few minutes at higher temperature on up to as long as about 48 hours at lower temperatures. Of course, concentration of reactants, pressure, proportion of free radical initiator, and the like also may influence reaction times, though reaction temperature usually will exert the greatest influence. Under preferred reaction conditions, reaction times typically will range from about 0.5 to about 1 hour. It should be noted that no detectable sulfinate-sulfonate mixture results from the instant reaction, though often such a mixture results when sulfonating linear olefins.

The product para-menth-1-ene-7-sulfonate salts can find wide use for their detergent properties, and as surfactants. Additionally, the sulfonate salts may be converted into their corresponding sulfonic acids by use of acid ion exchange chromatography, by use of protic acids, or by other conventional techniques. Substantial preservation of optical purity of an optically active β-pinene fed to the process in the product sulfonate salts is a valuable and unique feature of the present process. Such optical purity also can be preserved in the corresponding sulfonic acids which make them potential resolving agents. The para-menth-1-ene-7-sulfonate salts additionally can be converted into β-phellandrene according to process described in commonly assigned application U.S. Ser. No. 886,659, now U.S. Pat. No. 4,136,126 issued Jan. 23, 1979. In such process, β-phellandrene is prepared by heating a para-menth-1-ene-7-sulfonate salt at about 150° to 300° C. under non-acidic conditions.

The following examples show how the present invention can be practiced but should not be construed as limiting. In this application, all temperatures are in degrees Centigrade, and all ratios and percentages are on a molar basis, unless otherwise expressly indicated.

EXAMPLE 1

Into a pressure vessel was added β-pinene (1.21 moles), water (250 ml.), methanol (250 mol), sodium bisulfite (1.27 moles), and potassium nitrate catalyst (0.13 moles). This reaction mixture was heated at 110° C. while oxygen at 5 psig was passed into the reaction mixture. An exothermic reaction was observed within 10 minutes after commencement of the oxygen and the reaction pressure temporarily was increased by about 5–10 psig. After 4 hours reaction time, 392 grams of a white crystalline solid was recovered from the reaction mixture. This solid was recrystallized from 90% ethanol to yield 148.3 grams of recrystallized solid. This solid analyzed as para-menth-1-ene-7-sodium sulfonate (47.5% theory yield of the monohydrate of the sodium sulfonate product based upon β-pinene fed to the process) Complete recovery of the sodium sulfonate product is difficult due to its relatively high solubility in water. Exhaustive recovery procedures were not practiced in the Examples and likely all reported yields are lower than the actual yields.

Analytical results on the product are as follows: mp=200° up, slow decomposition, $[\alpha]_D = -64.0°(C=10)$ 1.00 N HCl. Found: C-46.79; H=7.48; S=11.73; Na-8.23%. Calculated for the monohydrate, $C_{10}H_{19}SO_4Na$: C=46.49; H=7.41; S=12.41; Na=8.9%. Analytical results on the p-chloro-s-benzylthiouronium salt were as follows: mp=180° C. Found: C=51.71; H=6.54; N=6.66; S=15.0; Cl=8.45%. Calculated for $C_{18}H_{27}O_3S_2N_2Cl$: C=51.60; H=6.45; N=6.69; S=15.31; Cl=8.48%. No sulfinate-sulfonate mixture was detected by conventional titration technique.

EXAMPLE 2

The procedure of Example 1 was repeated using 300 ml. each of water and methanol. The initial crude wet solid was washed with diethyl ether which removed 6.8 grams of oil containing various hydrocarbon rearranged by-products. The washed solid was recrystallized from 90% ethanol to yield 152.2 grams of solid (48.7% theory yield) which analyzed as hydrated para-menth-1-ene-7-sodium sulfonate salt.

EXAMPLE 3

The procedure of Example 2 was repeated with azobisisobutyronitrile radical initiator (0.006 moles) instead of oxygen. The recrystallized product (161.5 grams or 51.7% theory yield) analyzed to be pure para-menth-1-ene-7-sodium sulfonate.

EXAMPLE 4

The procedure of Example 2 was repeated without the potassium nitrate catalyst. Recrystallization of the crude product yielded 6.5 grams of para-menth-1-ene-7-sodium sulfonate (2.1% theory yield based on β-pinene fed to the process or 6.9% theory yield based on β-pinene converted in the process).

EXAMPLE 5

The procedure of Example 3 was repeated without the potassium nitrate catalyst. Unreacted β-pinene (35.2 grams or 21.4%) was extracted with ether from the crude solid reaction product. Recrystallization of the extracted solid yielded 84.6 grams of para-menth-1-ene-7-sodium sulfonate (27.6% theory yield based on β-pinene fed to the process or 34.7% theory yield based on β-pinene consumed in the process).

We claim:

1. The para-menth-1-ene-7-sulfonate salt of an alkali metal, alkaline earth metal, amine, zinc, or aluminum.
2. Para-menth-1-ene-7-sulfonic acid.
3. The para-menth-1-ene-7-sulfonate salt of claim 1 wherein said salt is a salt of an alkali metal, alkaline earth metal, zinc, or aluminum.
4. The para-menth-1-ene-7-sulfonate salt of claim 1 wherein said salt is a salt of triethanolamine.

* * * * *